United States Patent [19]

Childs

[11] 3,990,988
[45] Nov. 9, 1976

[54] CONSTANT BOILING ADMIXTURE
[75] Inventor: William V. Childs, Bartlesville, Okla.
[73] Assignee: Phillips Petroleum Company, Bartlesville, Okla.
[22] Filed: Nov. 13, 1975
[21] Appl. No.: 631,579

[52] U.S. Cl. .......................... 252/364; 252/DIG. 9; 252/171
[51] Int. Cl.² ........................ B01F 1/00; C23G 5/00
[58] Field of Search ............... 252/364, DIG. 9, 171

[56] References Cited
UNITED STATES PATENTS
2,409,859  11/1958  Horsfall ............................ 260/487
2,922,816  1/1960  MacMillan ........................ 260/544

FOREIGN PATENTS OR APPLICATIONS
536,387  1/1957  Canada

*Primary Examiner*—Benjamin R. Padgett
*Assistant Examiner*—Josephine Lloyd

[57]  ABSTRACT

A substantially constant boiling admixture of hexyl trifluoroacetate and 1-hexanol.

3 Claims, No Drawings

CONSTANT BOILING ADMIXTURE

FIELD OF THE INVENTION

The invention relates to a novel method of preparing high purity hexyl trifluoroacetate. In another aspect, it relates to a novel substantially constant boiling admixture as a composition of matter.

BACKGROUND OF THE INVENTION

Hexyl trifluoroacetate is a valuable feed in electrochemical fluorination processes. Hexyl trifluoroacetate as a feed in electrochemical fluorination cells produces perfluorohexanoyl fluoride which is important in the production of surfactants and antiwetting agents for treatment of fabrics.

However, in order to prepare commercially desirable yields of perfluorohexanoyl fluoride by electrochemical fluorination, avoiding side reactions and to reduce insofar as possible miscellaneous side products, it is important that the hexyl trifluoroacetate feedstock be prepared in as pure a state as possible.

BRIEF SUMMARY OF THE INVENTION

I have discovered a method of producing high purity hexyl trifluoroacetate without the use of chemicals other than the precursors, thus avoiding potential sources of product contamination.

In preparation of hexyl trifluoroacetate, hexanol is employed in reaction with a trifluoroacetate source, which can be trifluoroacetic acid or trifluoroacetic acid precursor. The reaction zone organic phase effluent comprises predominantly hexyl trifluoroacetate, together with unreacted hexanol, and water. The organic phase is distilled. Water, being lowest boiling, goes overhead. Thereafter, a hexyl trifluoroacetate/hexanol substantially constant-boiling admixture distills overhead until the hexanol is exhausted. Remaining is a highly pure hexyl trifluoroacetate with a purity which makes it an excellent feedstock for electrochemical fluorination.

DETAILED DESCRIPTION OF THE INVENTION

Hexanol is reacted with a trifluoroacetate source, which can be trifluoroacetic acid or acid precursor or mixtures, to form hexyl trifluoroacetate. Suitable acid precursors include trifluoroacetyl halides and trifluoroacetic anhydride. Suitable trifluoroacetyl halides include the presently preferred fluoride, as well as the chloride and bromide.

In a typical method of preparation, a trifluoroacetate source is reacted with n-hexanol employing a mole ratio of about 1:10 to 10:1 preferably 0.5:1 to 10:1, hexanol:trifluoroacetate source, more preferably about 0.75:1 to 2:1. Esterification is accomplished by contacting the components in a suitable esterification means, employing a temperature such as about −20° to 100° C, more preferably about 0° to 50° C. Atmospheric pressure generally is employed, though subatmospheric or superatmospheric pressure such as about 10 KPa to 10 MPa can be employed if desired, e.g., to alter reflux temperature.

If desired, the esterification reaction can be catalyzed by materials well known in the art as esterification catalysts such as strong acids, for example, sulfuric acid. Time does not appear critical in the process, and the esterification process can be continued for a suitable time, though an exemplary time would be from a few minutes to several days such as 24 to 48 hours or more.

Since unesterified reactants can be separated, or recovered and recycled to the esterification zone where suitable, total esterification is unnecessary. Hence the esterification reaction can be continued until complete or until any desired degree of esterification is attained. It sometimes is desirable to remove overhead continuously a portion of the reaction products, such as water from the reaction of 1-hexanol with trifluoroacetic acid, in order to drive the reaction to a higher degree of completion.

The product stream from the esterification step comprises primarily the ester hexyl trifluoroacetate, remaining unreacted hexanol, and byproducts of the esterification either water and trifluoroacetic acid or hydrogen halide or mixtures thereof, plus any unreacted trifluoroacetic acid or acid precursor. If the trifluoroacetate source is the anhydride in whole or part, there will be quantities of acid in the reaction product mixture. If an acid halide is the source there will be amounts of hydrogen halide HX in the reaction product admixture.

After esterification is completed, or the degree of desired esterification obtained, the esterification zone effluent then is treated so as to remove at least a portion of the byproducts of esterification, and unreacted acid or acid precursor. This can be by one or more washing steps if desired, such as washing with water, or cold saturated salt solution to remove acidic components and to assist in salting-out of water from the organic phase. The washing step can be omitted in most instances, particularly where the preferred reactants 1-hexanol and trifluoroacetic acid have been employed. In some instances, such as when the preferred reactants have been employed, sufficient byproduct water may be formed as to permit phase separation of the aqueous phase from the substantially organic phase.

Thereafter, or directly if the washing step is omitted, the esterification reaction product organic phase stream now comprising hexyl trifluoroacetate, unreacted 1-hexanol, and residual water of reaction and/or residual water from the washing step, is fractioned in a suitable distillation means.

Optionally, the organic phase product stream comprising hexyl trifluoroacetate, 1-hexanol, and water, can be dried, such as over anhydrous magnesium sulfate or anhydrous potassium carbonate to remove a portion of the water prior to the distillative step.

In the distillative step, water being the lowest boiling component, goes overhead and can be discarded. Thereafter, a substantially constant boiling stream of hexyl trifluoroacetate/1-hexanol is received overhead, and can be recycled to the esterification zone, if desired. The substantially constant boiling stream continues to distill until the 1-hexanol is exhausted from the distillation means. Thereafter, the kettle bottoms or heavies product is a high purity hexyl trifluoroacetate. The distillative separation does not have to be precise, simply continuing distillation until hexanol in the kettle product is exhausted, and if any hexyl trifluoroacetate does go overhead after the azeotrope, such can be simply returned to the esterification zone and recycled.

The bottoms product then is recovered as a highly pure hexyl trifluoroacetate useful in feedstock for electrochemical fluorination preparation of perfluorohexanoyl fluoride. If desired the bottoms product, hexyl trifluoroacetate, can be even further purified by distillation following exhaustion of 1-hexanol in the fractionation zone, though by my process purity already is such that this is usually unnecessary.

Methods of electrochemical fluorination are well known and do not form a part of this invention, being described in such U.S. Pat. Nos. as 3,511,760, 3,511,761 and 3,511,762.

EXAMPLES

The following examples and operational data are presented to assist a further understanding of my invention, and is particularly directed to those skilled in the art to which it appertains. Particular conditions, proportions, and the like, are designed to be exemplary and not limitative of the scope of my invention.

EXAMPLE I

Hexyl alcohol (1-hexanol) 205 g (2 mol), and trifluoroacetic acid, 250 g (2.2 mol), were admixed and allowed to react at a temperature of about 25° C for approximately 48 hours employing a 1 liter glass reactor.

Examination of the reaction mixture indicated a two-phase product, with the upper organic phase identified by gas-liquid chromatrography as primarily hexyl trifluoroacetate together with 1-hexanol. The lower water phase was substantially removed by a separatory funnel. The organic phase was washed three times with 0.2 volume of a saturated sodium chloride/distilled water admixture to remove acidic components and to assist water separation. The washed organic phase then was dried over magnesium sulfate, and thereafter the magnesium sulfate residue was filtered off. Examination determined that the esterification reaction had not reached the desired degree of completion. Therefore, to the product so obtained was added an additional 80 cc (1.1 mole) trifluoroacetic acid and allowed to react for further esterification. The resulting esterification product mixture then was washed three times with 0.2 volume of ice cold saturated sodium chloride/water admixture which removed acidic components and assisted separation of phases. The aqueous layer was discarded, and the organic layer was dried over magnesium sulfate, and thereafter dried over potassium carbonate. This drying step is convenient, but not necessary.

The organic phase admixture so obtained, comprising hexyl trifluoroacetate, residual 1-hexanol, and minor amounts of water, was charged to a 250 mm glass distillation column packed with Monel rectangular prisms measuring 2.3 mm × 4.4 mm × 4.4 mm.

Distillation was commenced and the following data and cuts were obtained:

| Cut No. | Temperature, °C (740 mm Hg) | |
|---|---|---|
| | Head | Pot |
| 1 | 142–146 | 152–153 |
| 2 | 147 | 152 |
| 3 | 147 | 152 |
| 4 | 147 | a |
| 5 | 147 | a | a) Not recorded

The several fractions were each examined by gas-liquid chromatography. Cut No. 1 (fraction No. 1) contained about 95.7 area percent (96.2 weight percent) hexyl trifluoroacetate, and about 4.3 area percent (3.8 weight percent) 1-hexanol. Analysis indicated that this fraction contained my novel azeotrope plus extra ester because the distillation had been continued a little too long.

The other fractions, Fractions 2, 3, 4, and 5, each analyzed 99.7, 99.7, 99.9, and 99.9 area percent hexyl trifluoroacetate, corresponding respectively to 99.8, 99.8, 99.9, and 99.9 weight percent very high purity hexyl trifluoroacetate. This run demonstrates the high efficiency of my process and the capability thereof to produce a valuable high-purity hexyl trifluoroacetate feedstock. This run also demonstrates the usefulness of the azeotrope of n-hexanol with hexyl trifluoroacetate which I have discovered.

EXAMPLE II

In a further investigation to determine the precise nature of the substantially constant boiling admixture of azeotropic composition itself, an admixture was prepared of about 97.66 g (0.4932 mole) trifluoroacetate and 80.26 g (0.7856 mole) 1-hexanol. The admixture was charged to a kettle, and distilled employing a 250 mm glass column packed with Monel rectangular prisms measuring 2.3 mm × 4.4 mm × 4.4 mm. The first several milliliters overhead were discarded. The overhead sample distilled primarily at 142.5° C. at substantially atmospheric pressure, 740 mm Hg at time of measurement, and GLC analysis indicated 79.3 weight percent hexyl trifluoroacetate and 20.7 weight percent n-hexanol. This was the azeotropic composition.

Constant boiling admixtures are liquid mixtures of two or more substances which mixtures behave like a single substance in that the vapor produced by partial evaporation or distillation has the same composition as does the liquid, i.e., the admixtures distill without change in composition. Constant boiling compositions characterized as azeotropes exhibit either a maximum or minimum boiling point as compared with that of nonazeotropic mixtures of the same substances. It is not possible to predict what two or more substances will combine to form azeotropes, as the resultant mixture must exhibit non-ideal phase behavior in order for an azeotrope to form, and non-ideal phase behavior is unpredictable.

At differing pressures, the composition of a given azeotrope will vary, at least slightly, and changes in distillation pressures also change, at least slightly, the distillation temperatures. Thus, an azeotrope of A and B represents a unique type of relationship but with a variable composition depending upon temperature and/or pressure.

It is possible to fingerprint, in effect, a constant boiling admixture, which may appear under varying guises depending on the conditions chosen, by any of several criteria: The composition can be defined as an azeotrope of A and B, since the very term "azeotrope" is at once both definitive and limitative, requiring that A and B indeed form this unique composition of matter which is a constant boiling admixture. Or, the composition can be defined as a particular weight percent relationship or mole percent relationship of A:B, while recognizing that such specific values point out only one particular such relationship and that in actuality a series of such relationships represented by A:B actually exist for a given azeotrope, varied by influence of distillative conditions the temperature and pressure relationship. Or, recognizing that the azeotrope A:B does represent just such a series of relationships, the azeotropic series represented by A:B can be characterized by defining the composition as an azeotrope characterized by a boiling point at a given pressure, thus giving identifying characteristics without unduly limiting the scope of the invention by a specific numerical composition, which is limited by and is only as accurate as the analytical equipment available. The same considerations are applicable to both binary azeotropes A:B and to ternary azeotropes A:B:C.

The disclosure, including data, illustrate the value and effectiveness of my invention. Exemplary data, the knowledge and background of the field of the invention and general principles of chemistry and other applicable sciences, have formed the basis from which the broad description of the invention including the ranges of conditions have been developed which have formed the basis for my claims here appended.

I claim:

1. A constant boiling admixture characterized as an azeotrope of about 79.3 weight percent hexyl trifluoroacetate and 20.7 weight percent 1-hexanol at substantially atmospheric pressure.

2. The constant boiling admixture of claim 1 characterized by a boiling point of about 142.5° C at substantially atmospheric pressure.

3. The constant boiling admixture of claim 1 characterized by a boiling point of about 142.5° C at a pressure of about 740 mm Hg.

* * * * *